United States Patent [19]

Kameswaran

[11] Patent Number: 4,506,097

[45] Date of Patent: Mar. 19, 1985

[54] METHOD FOR THE RACEMIZATION OF (2)-2-(4-DIFLUOROMETHOXYPHENYL)-3-METHYLBUTYRIC ACID

[75] Inventor: Venkataraman Kameswaran, Princeton Junction, N.J.

[73] Assignee: American Cyanamid Co., Stamford, Conn.

[21] Appl. No.: 488,476

[22] Filed: Apr. 25, 1983

[51] Int. Cl.³ .............................................. C07B 20/00
[52] U.S. Cl. ...................................... 562/401; 560/55; 562/465
[58] Field of Search ................... 562/401, 465; 560/55

[56] References Cited

U.S. PATENT DOCUMENTS 4,199,595  4/1980  Berkelhammer et al. ........ 560/55 X
4,237,313  12/1980 Higo et al. ........................... 562/401
4,245,116  1/1981  Ohno et al. ......................... 562/401

*Primary Examiner*—Natalie Trousof
*Assistant Examiner*—Vera C. Clarke
*Attorney, Agent, or Firm*—Estelle J. Tsevdos; Alphonse R. Noë

[57] ABSTRACT

A method for the racemization and hydrolysis of alkyl esters of (−)-2-(4-difluoromethoxyphenyl)-3-methylbutyric acid, followed by the resolution of said resulting racemic acid into its optically active components via salts prepared from the same with optically active amines and recovery of the dextrorotatory (+) isomer therefrom. The present invention also relates to insecticidal pyrethroids prepared from (+)-2-(4-difluoromethoxyphenyl)-3-methylbutyric acid.

4 Claims, No Drawings

METHOD FOR THE RACEMIZATION OF (2)-2-(4-DIFLUOROMETHOXYPHENYL)-3-METHYLBUTYRIC ACID

The invention herein described relates to a method for the racemization and hydrolysis of alkyl esters of (−)-2-(4-difluoromethoxyphenyl)-3-methylbutyric acid in one reaction system; followed by the resolution of said resulting racemic acid into its optically active components via salts prepared from said racemic acid with optically active amines, and subsequent recovery of the desired dextrorotatory isomer.

By way of background, the racemic 2-4(4-difluoromethoxyphenyl)-3-methylbutyric acid, and especially the dextrorotatory (+) isomer thereof, are useful and valuable intermediates for the preparation of pyrethroid-type pesticides. This racemic acid and its optical isomers may be represented by structural formula (I) wherein the asterisk indicates the location of the chiral center in said structure:

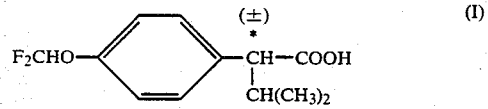

The formula (I) acid, analogs thereof and the pesticidal pyrethroids derived therefrom are disclosed and claimed in U.S. Pat. No. 4,199,595, incorporated herein by way of reference.

In light of the foregoing discussion of the desirability of obtaining pyrethroid pesticides for control of noxious pests, it is necessary to obtain the chemical intermediates which are involved in the synthesis of these products. Accordingly, an object of this invention is to provide a method for the racemization and hydrolysis of alkyl esters of (−)-2-(4-difluoromethoxyphenyl)-3-methylbutyric acid, the resolution of the resulting racemic acid into its optically active components, and recovery of the desired destrorotatory (+) isomer. Thus, a method is provided for the preparation of (+)-2-(4-difluoromethoxyphenyl)-3-methylbutyric acid. This object is manifest in the following description and particularly delineated in the appended claims.

One of the desirable pyrethroid pesticides of U.S. Pat. No. 4,199,595 is prepared from the formula (I) acid as follows:

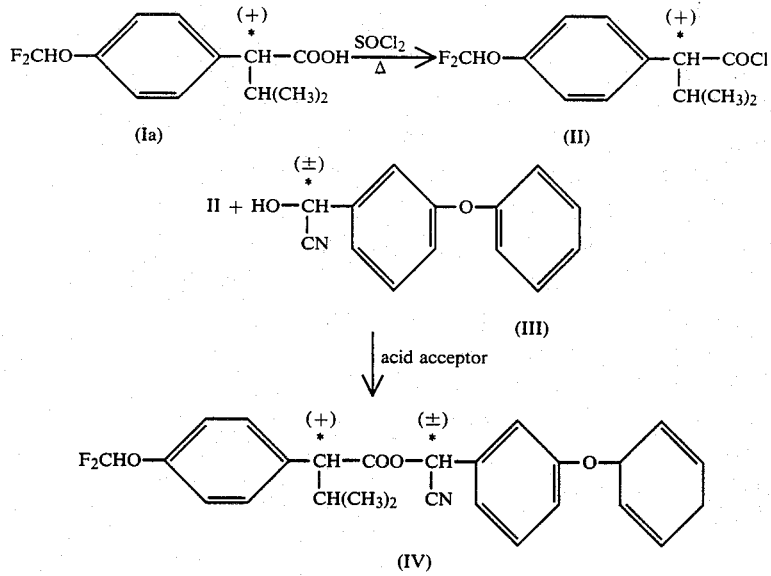

The structural formula (IV) pesticide has two chiral centers which are indicated above by asterisks. Accordingly, the formula (IV) pesticide is a two isomer mixture derived from the (+) acid and the (±) alcohol as illustrated above.

In the course of resolving the formula (I) racemic acid to obtain the desired (+) acid required in the above reaction sequence, a significant amount of (−)-acid of formula (I) is also obtained. It is desirable to recycle the above (−)-acid via a racemization-resolution process in order to obtain additional amounts of the (+)-isomer of said formula (I) acid.

Conveniently, one molar equivalent of a $C_1$–$C_3$ alkyl ester [preferably a methyl ester of a (−)-enriched formula (I) acid] is dissolved in an anhydrous $C_1$–$C_3$ alcohol (preferably methanol). Next, about one to two molar equivalents (preferably 1.25 to 1.50 molar equivalents) of sodium or potassium hydroxide is added. The reaction mixture is then heated at a temperature of about 60° to 100° C. (preferably 68° to 72° C.), or at the boiling point of the alcohol selected, for about two to ten hours (preferably six to seven hours) or until the reaction is essentially complete. Next, if so desired, the solvent is removed, as under vacuum.

The residue is dissolved in water and the racemic acid mixture precipitated with a strong mineral acid (i.e., hydrochloric acid). This reaction sequence is illustrated as follows:

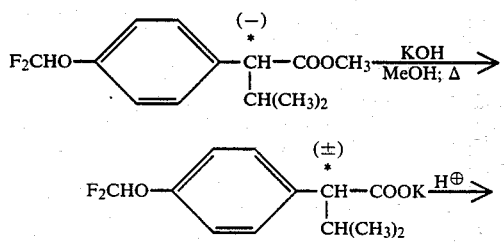

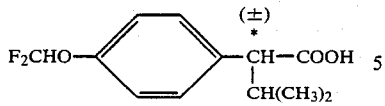

The racemic (±) acid of formula (I), obtained as illustrated above, may be resolved as follows: One molar equivalent of the racemic acid is dissolved in a $C_1$-$C_3$ aliphatic alcohol (i.e., 2-propanol), the solution is heated to the boiling point of the alcohol selected, and a 0.5 molar equivalent of (−)-α-phenethylamine is added slowly. On completion of the addition, the mixture is heated briefly to complete the salt formation, cooled, and the (+)-acid salt of (−)-amine is isolated by standard laboratory procedures. The free (+) acid is then regenerated from the above salt and used in the preparation of formula (IV) pesticide; while the (−)-acid, recovered from the racemate, is recycled again as described above.

The pyrethroid pesticide of formula (IV) and other pyrethroids prepared from formula (I) acid are highly effective as contact and stomach poisons for ixodide ticks and for a wide variety of insects, particularly dipterous, lepidopterous, coleopterous and homopterous insects. These pesticidal compounds also exhibit extended residual insecticidal activity on plant tissue.

To control insect pests, (including soil insects), which attack growing plants and/or harvested crops, (including stored grain), the insecticidal compounds of formula (IV) and others prepared from said formula (I) acid may be applied to the foliage of plants, the insect's habitat and/or the insect's food supply. Generally, the active compound is applied in the form of a dilute liquid spray. However, it may also be applied as an aerosol, a dust, a granular, or a wettable powder formulation.

Liquid sprays which are particularly useful are oil sprays and emulsifiable concentrates which can be further diluted for application. Although they are prepared as liquid concentrates for convenience in handling and shipping, these formulations are usually dispersed in water at the site of their use and then applied as a dilute spray to the plant foliage, soil or surface of the area being treated.

A typical emulsifiable concentrate useful for protecting a variety of crops such as cereals, cole crops, cucurbits, corn, cotton, tobacco, soybeans, ornamentals, shrubs, and the like, may comprise about 20% by weight of the active agent; 4% by weight of an emulsifying agent, conventionally employed in the preparation of pyrethroid formulations; 4% by weight of a surfactant; 25% by weight of an organic solvent such as cyclohexanone; and about 47% by weight of a petroleum solvent having a minimum aromatic content of about 83 volume %.

The invention is further described and illustrated by the examples set forth below which are not intended to be limitative thereof.

EXAMPLE 1

One-step racemization and hydrolysis of the methyl ester of (−)-enriched-2-(4-difluoromethoxyphenyl)-3-methylbutyric acid To a solution of 243.0 g {0.941 mol; $[\alpha]_D = -21.22°$; (CHCl$_3$, c=1.753 g/100 ml)} of methyl 2-(4-difluoromethoxyphenyl)-3-methylbutyrate in 972 ml of anhydrous methanol is added slowly 77.6 g (65.98 g real) of potassium hydroxide pellets (1.176 mol; or 125 mol %). The reaction mixture is refluxed at 68° to 70° C. for six hours and allowed to cool slowly to room temperature. The solvent is then removed under vacuum. The residue is washed with 400 ml cold water and extracted twice with hexane (400 ml and 200 ml). The aqueous phase is acidified with concentrated hydrochloric acid, using ice to keep the mixture cool. The acidified mixture is extracted twice with hexane (2×400 ml). The hexane solution is washed with water, saturated brine, dried over sodium sulfate, and evaporated to afford 185.2 g of an oil which solidifies on standing {80.7%; $[\alpha]_D = -1.4°$ (CHCl$_3$, c=1.059 g 100 ml)}. The product contains approximately 51.6% of (−)- and 48.4% of (+)-2-(4-difluoromethoxyphenyl-3-methylbutyric acid.

EXAMPLE 2

Preparation of the methyl ester of (−)-enriched-2-(4-difluoromethoxyphenyl)-3-methylbutyric acid A solution of 250 g {1.023 mol; $[\alpha]_D = -21.04°$ (CHCl$_3$, c=2.385 g/100 ml)} of (−)-enriched-2-(4-difluoromethoxyphenyl)-3-methylbutyric acid in 1000 ml of toluene and 0.5 ml DMF is heated at 70° C. and 121.7 g (1.023 mol; 74.7 ml) of thionyl chloride is added over 30 minutes at such a rate as to provide control over the evolution of gases. After the addition is completed, the reaction mixture is heated at 100° C.

After one hour, the mixture is cooled to 15° to 20° C. and 79.8 g (82.3 ml) pyridine (1.023 mol) is added. The reaction mixture is stirred and 39.3 g (49.8 ml; 1.228 mol; or 125 mol %) of anhydrous methanol is added at a rate sufficient to maintain the temperature of the mixture below 40° to 45° C. After the addition is completed, the reaction mixture is stirred for 15 minutes, cooled, and diluted with water. The organic phase is separated and washed in succession with 400 ml of 10% hydrochloric acid, 400 ml of 5% sodium hydroxide, and twice with water (2×400 ml). The solution is then dried over sodium sulfate and evaporated to afford 243.7 g of a brown oil, the product {$[\alpha]_D = -21.22°$ (CHCl$_3$, c=1.753 g/100 ml)}.

EXAMPLE 3

Resolution of racemic 2-(4-difluoromethoxyphenyl)-3-methylbutyric acid

A solution of 200 g (0.819 mol) of racemic (±) 2-(4-difluoromethoxyphenyl)-3-methylbutyric acid in 1000 ml (5 ml/g acid) of 2-propanol is heated to 80° C., stirred, and 49.6 g (0.409 mol; 0.5 mol/1.0 mol acid) of (−)-α-phenethylamine is added dropwise over a 10 to 15 minute period. The reaction mixture is held at 80° C. for 15 minutes, and then cooled to 70° C. to initiate crystallization. After one hour at 70° C., the mixture is cooled slowly (over three to four hours) to room temperature and is filtered. The isolated solid is washed with 200 ml of 2-propanol and dried under vacuum at 60° C. to afford 104.8 g of the (+)-acid salt of the (−)-amine; mp 178°-180° C. (70.1% yield).

The above salt is then digested with 300 ml of 10% hydrochloric acid and the aqueous mixture is extracted with methylene chloride (2×150 ml). The organic phase is washed with water (2×100 ml) and dried over sodium sulfate. The solvent is removed under vacuum to yield 70.2 g of a yellow liquid, $[\alpha]_D = +34.3°$ (CHCl$_3$, c=1.212 g/ml); 89.1% of which is the (+)-isomer.

EXAMPLE 4

Preparation of α-cyano-3-phenoxybenzyl-2-(4-difluoromethoxyphenyl)-3-methylbutyrate A solution of 2-(4-difluoromethoxyphenyl)-3-methylbutyryl chloride (4.58 mmol; prepared by the method of Example 2) in ether (5 ml) is added to an ether (20 ml) solution of α-cyano-3-phenoxybenzyl alcohol (4.58 mmol) and pyridine (0.5 ml). The mixture is stirred overnight and filtered. Filtrate and washing are evaporated. The residual oil is purified on 5×2 mm silica gel plates using 1:1 methylene chloride:hexane eluent to afford the title product.

EXAMPLE 5

Insecticidal Activity

The insecticidal activity of the compound of the present invention is demonstrated by the following tests.

The procedures employed for evaluation against mosquito larvae, Mexican Bean Beetles and Southern Armyworms are as follows:

Malaria Mosquito, *Anopheles quadrimaculatus* (Say)

One milliliter of a 35% water/65% acetone solution containing 300 ppm of test compound is pipetted in a 400 ml beaker containing 250 ml of deionized water and stirred with the pipette, giving a concentration of 1.2 ppm of the test compound. Aliquots of this solution are taken and further diluted to 0.4, 0.04 and 0.004 ppm. A wax paper ring (0.6 cm wide) sufficient to fit inside the beaker is floated on the surface of the test solution to keep the eggs from floating up the meniscus curve and drying out on the side of the glass. A spoon made of screen is used to scoop up and transfer about 100 eggs (0 to 24 hours old) into the test beaker. After two days at 80° F. and 50% relative humidity, observations of hatching are made. Percent mortality records are presented in Table I.

Mexican Bean Beetle, *Epilachna varivestis* (Mulsant)

Sieva lima bean plants (2 per pot) with primary leaves 7.5 to 10 cm long, are dipped in solutions containing 300, 100, 10 or 1 ppm of test compound and set in the hood to dry. One leaf is removed from a plant and placed in a 10 cm petri dish containing a moist filter paper on the bottom and 10 last-instar larvae (13 days from hatching). The day after treatment, another leaf is removed from the plant and fed to the larvae after removing the remains of the original leaf. Two days after treatment, the third leaf is fed to the larvae. This is usually the last required feeding. The fourth leaf is used on the third day after treatment if the larvae have not finished feeding. The test is now set aside and held until adults have emerged, usually in about nine days after treatment began. After emergence is complete, each dish is examined for: dead larvae, pupae or adults; deformed pupae or adults; larval-pupal intermediates or pupal-adult intermediates; or any other interference with normal molting, transformation and emergence of pupae or adults.

Data obtained are reported in Table I.

Southern Armyworm, *Spodoptera eridania* (Cramer)

Sieva lima bean plants having with two expanded 7.5 to 10 cm primary leaves are dipped for three seconds with agitation in the treatment solutions and are then set in a hood to dry. After the leaves are dry, they are excised. Each excised leaf is placed in a 10 cm petri dish containing a piece of moist filter paper and 10 third-instar southern armyworm larvae approximately 1 cm long. The petri dishes are covered and placed in a holding room for two days at a temperature of 80° F. and 50% relative humidity.

Mortality counts are made after two days. Results obtained are presented in Table I.

TABLE I

| | Insecticidal Evaluation | | | | | | | | | | |
|---|---|---|---|---|---|---|---|---|---|---|---|
| | | % Mortality | | | | | | | | | |
| | | Mosquito Larvae | | | | Southern Armyworm | | | Mexican Bean Beetle | | |
| Compound | | 1.2 ppm | 0.4 ppm | 0.04 ppm | 0.004 ppm | 1000 ppm | 100 ppm | 10 ppm | 300 ppm | 100 ppm | 10 ppm | 1 ppm |
| 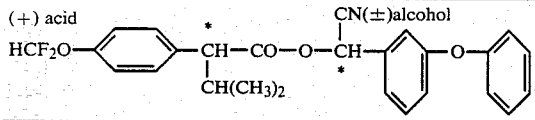 | | 100 | 100 | 100 | 100 | 100 | 100 | 100 | 100 | 100 | 100 | 50 |

What is claimed is:

1. A method for the racemization and hydrolysis of alkyl esters of (−)-2-(4-difluoromethoxyphenyl)-3-methylbutyric acid comprising: reacting one molar equivalent of a C$_1$-C$_3$ alkyl ester of (−)-2-(4-difluoromethoxyphenyl)-3-methylbutyric acid with one to two molar equivalents of sodium or potassium hydroxide in the presence of anhydrous C$_1$-C$_3$ alcohol at a temperature from about 60° to 100° C. or at the boiling point of the alcohol selected; for a period of time from about two to ten hours or until the reaction is essentially complete.

2. A method according to claim 1, wherein the amount of sodium or potassium hydroxide is about 1.25 to 1.50 molar equivalents; the alcohol is methanol; the reaction temperature is about 68° to 70° C.; and the reaction time is about six to seven hours.

3. A method according to claim 2, wherein the ester of the (−)-2-(4-difluoromethoxyphenyl)-3-methylbutyric acid is the methyl ester.

4. A method according to claim 3, wherein said methyl ester is reacted with about 1.25 molar equivalents of potassium hydroxide.

* * * * *